United States Patent [19]

Gestrelius et al.

[11] 4,380,552
[45] Apr. 19, 1983

[54] METHOD OF DEACIDIFYING WINE AND COMPOSITION THEREFOR

[75] Inventors: Stina M. Gestrelius, Lund, Sweden; Jörgen H. Kjaer, Copenhagen, Denmark

[73] Assignee: Novo Industri A/S, Bagsvaerd, Denmark

[21] Appl. No.: 201,227

[22] Filed: Oct. 27, 1980

[51] Int. Cl.$^3$ ............... C12P 7/56; C12N 11/10; C12N 1/36; C12G 1/00
[52] U.S. Cl. ......................... 426/52; 426/61; 426/592; 435/139; 435/178; 435/245; 435/260
[58] Field of Search ............ 426/12, 15, 51, 52, 426/61, 592; 435/139, 174, 182, 245, 260, 177, 178

[56] References Cited

U.S. PATENT DOCUMENTS 3,733,205  5/1973  Shovers et al. .................. 426/62

OTHER PUBLICATIONS

Kunkee, R. E., "Chemistry of Winemaking", (A. D. Webb, ed.), *Advances in Chemistry Series*, No. 137, p. 137 (1974).

Kierstan, M. et al., 'The Immobilization of Microbial Cells, Subcellular Organelles, and Enzymes in Calcium Alginate Gels', *Biotechnology and Bioengineering*, vol. 19, 1977, pp. 387–397.

*Primary Examiner*—Raymond N. Jones
*Assistant Examiner*—Elizabeth J. Curtin
*Attorney, Agent, or Firm*—Fidelman, Wolffe & Waldron

[57] ABSTRACT

Deacidifying wine by passage through an alginate gel containing living cells of *Leuconostoc oenos* therein. To ensure maximum viability, the alginate gel is stored in a resting medium, preferably sterile grape juice containing 5–12% ethanol. Before deacidifying wine the immobilized cells are conditioned to a wine milieu.

6 Claims, No Drawings

METHOD OF DEACIDIFYING WINE AND COMPOSITION THEREFOR

This invention relates to the deacidification of wine and in particular to carrying out malolactic fermentation under controlled continuous conditions by an immobilized microorganism. Specifically, the wine comes into contact with living cells of *Leuconostoc oenos* immobilized in alginate beads, a novel malolactic enzyme.

INTRODUCTION

As is well known in the art the malolactic fermentation takes place in malate-rich wines subsequent to the usual yeast alcoholic fermentation of grape juice that formed the wine. Since the malolactic fermentation converts the dicarboxylate L-malate to the mono-carboxylate L-lactate, this loss of a carboxyl acid group decreases the acidity of the wine. Indeed, (spontaneous or initiated) malolactic fermentation of malate-rich wines has been widely employed as a way to decrease acidity in the relatively acid wines from cool climatic regions.

Deliberately carrying out a malolactic fermentation in the vat will stabilize wine by insuring that secondary fermentation (i.e., the malolactic fermentation) will not take place later in the bottle. In addition, the malolactic fermentation may increase the flavor complexity of the wine.

By and large, in Germany and Switzerland white wines are caused to undergo malolactic fermentation in order to reduce acidity. On the other hand, California white wines frequently are not allowed to undergo such conversion. In the instance of red-wines, including the wines from California, South Africa, mid-France, Australia and New Zealand, a serious problem is the fact that the malolactic fermentation may not take place before bottling or that only a slow or delayed spontaneous malolactic fermentation takes place prior to bottling, since especially the wines with moderately high pH e.g., 3.7–3.8 may undergo the malolactic fermentation in the bottle, if no precaution is taken.

For a typical prior art spontaneous malolactic fermentation procedure, the new wine is kept two months or more at somewhat raised temperatures such as 70° F. and at a low SO$_2$ content. Under such conditions spontaneous malolactic fermentation often starts normally but sometimes stops long before completeness. (A reasonable measure for completeness of the malolactic conversion is a malate content in the wine of less than about 100 ppm.)

Inoculation of wine, for example with Leuconostoc or Pediococci species, to induce malolactic fermentation has been tried at pH 3.5 and 3.8 with some success.

By and large, the art accepts that malolactic fermentation of wine offers quality advantages. After such fermentation the wines are more harmonious, smoother, and biologically more stable. Fortunately, in many instances the malolactic fermentation is spontaneous, commencing either immediately after the original alcoholic fermentation or some weeks later, and continues to completeness. Microbial examinations of wines carried out while a spontaneous malolactic fermentation is taking place has established that species of diverse microorganisms may be involved. Most important are *Leuconostoc oenos, Lactobacillus hilgardii, Lactobacillus brevis, Pediococcus pentosaceus*, and *Pediococcus cerevisiae*. In addition, some Schizosaccharomyces species such as *Sz. pombe* are able to accomplish malate decomposition during a pre-fermentation of must.

Wine is a harsh growth medium for microorganisms, having a low pH, pH 3–4, as much as 10–14% ethanol content and 50–250 mg total SO$_2$ per liter, whereof 0–100 mg SO$_2$/liter is free SO$_2$. As a result, bacterial growth is uncertain and is slow when such occurs. As has been pointed out, spontaneous malolactic fermentation is sometimes incomplete, or may not occur.

Suggestions have even been made, of course, to separate bacterial growth from the malolactic activity of the microorganism. This can be accomplished by adding large amounts of resting microorganism cells to the wine, or by passing the wine through a reactor containing either living immobilized cells or appropriate enzymes obtained from the microorganism. Since the present invention relates to employment of living cells in an immobilized form for conduct of a malolactic conversion, it is worthy of note that viable Lactobacillus cells immobilized in an acrylic gel have been suggested by German Offenlegungsschrift No. 2,633,076 for the malolactic conversion.

BRIEF STATEMENT OF THE INVENTION

The present invention relates a composition comprising alginate gel particles with living cells of *Leuconostoc oenos* encapsulated therein immersed in an aqueous medium suited to maintaining viability of the microorganism, to the method of preparing such immobilized microorganism form, and to conduct of malolactic fermentation therewith.

The aqueous medium or resting medium wherein the particulate alginate gel remains stored until used is preferably a growth medium for the microorganism, desirably a sterile growth medium. One preferred resting medium is grape juice; more preferred is grape juice containing 5–12% ethanol. The purpose of the resting medium is to ensure the greatest proportion of viable cells in the alginate gel. The term "resting medium" is employed herein to denote an aqueous solution or medium adopted for maintaining viability.

This invention also is directed to the method of employing living *Leuconostoc oenos* cells encapsulated in a particulate alginate gel, preferably in the form of alginate beads, in a continuous bed or column process for conduct of the malolactic fermentation.

Thus, alginate particles containing the microorganism cells and the resting medium in which the particles have been stored are poured into a column, and thereafter, the aqueous medium is displaced by wine. Then wine is passed through the column at a rate appropriate to the fermentative conversion of the malic acid content to lactic acid during passage through the column. To the extent necessary, the living microorganism cells are acclimatized to the wine milieu during the course of substituting wine for the resting medium. Acclimatizing is particularly important should the strain of the *L. oenos* immobilized in the alginate gel be sensitive to the presence of sulphur dioxide in the wine.

DETAILED DISCUSSION OF THE INVENTION

The Microorganism

As has already been pointed out the present invention is directed to carrying out the malolactic conversion with living cells of *Leuconostoc oenos immobilized in a particulate alginate gel. Only a pure strain malolactic fermentation consistently produces organoleptically satis-*

*factory wines* and *L. oenos* is generally considered as being the best species for the conversion. Other microorganisms generate fermentation by-products such as diacetyl, $H_2S$ or acetic acid, all of which reduce the quality of the wines, sometimes considerably.

The conversion of malic acid to lactic acid involves an enzyme mechanism that is known to be NAD dependent and need for the cofactor i.e., NAD, all of which together with the rapid disappearance of NAD in the pH 3-4 wine milieu renders the enzyme content of nonviable cells largely useless for large scale conduct of a malolactic conversion. Accordingly, emphasis herein is placed on retaining a maximum proportion of viable cells (in the alginate gel immobilized *L. oenos* employed) for the conversion.

Another aspect of the practice of the present invention is that the main bacterial growth i.e., the proliferation of microorganism cells, is separated from application of the malolactic activity of the cells to wine. As has already been pointed out, wine is a poor growth medium for microorganisms. Accordingly, the practical situation is cultivation of the microorganism in a more suitable growth medium than wine, then the cells are recovered from the growth medium and transferred to wine, frequently at some later date and often at a different locale. In consequence, to the extent possible, the microorganism cells must not only be alive when recovered from their growth medium, but must remain viable throughout an immobilization process, some storage in immobilized form, and during shipment. Since *L. oenos* is anaerobic the inherently low oxygen tension inside the alginate gel particles wherein the microorganism cells are immobilized is not disadvantageous (as to long continued cell viability).

Detailed discussion of *L. oenos* is not required here since the malolactic activity of this microorganism species is well known in the art and several strains thereof have been suggested for use in wine deacidification, including "Teufen" from Dr. K. Mayer, Eidgenössische Forschungsanstalt für Obst-, Wein- und Gartenban, Wädenswil, Switzerland, DSM 20252, see Garvie, J. Gen. Microbiol. 1967 Vol. 48, 431-438), Leuco Start TM (Tri Bio Laboratories, State College, PA), and ML-34 from University of California, Davies (Ingraham et al., 1960, Am. J. of Enol. Vitic. 11; 1-4).

Immobilization

Subsequent to cultivation in its own growth medium and recovery therefrom, the *L. oenos* cell concentrate is dispersed in a solution of sodium or potassium alginate.

The concentration and relative proportions of alginate and *L. oenos* cells are somewhat arbitrary. Alginate solutions containing from 1-8% w/w of sodium or potassium alginate may be formed into gel particles of adequate stability for the malolactic conversion, and this range is preferred. Use of from 0.1-5 grams of *L. oenos* cells per gram of sodium or potassium alginate result in a gel product suitable for the malolactic conversion, and these proportions are contemplated herein. The preferred relative proportion is 0.2-1 gram of cells per gram of the alginate.

The particle size of the alginate gel affects the malolactic conversion. Small particle size provides for good mass transfer within the wine solution, but at some risk of clogging up a bed of particles. Large particle size offers superior physical stability for the gel particle bed, but at the expense of poor mass transfer characteristics.

For alginate gel in bead form, a 1-4 mm diameter range is a preferred particle size range.

To form an alginate gel in particulate form, the microorganism cell suspension alginate solution is dripped, or pumped or otherwise added to a concentrated aqueous solution of a non-toxic divalent cation, such as calcium chloride. The salt solution promptly reacts with the alginate solution precipitating calcium alginate as a gel, which gel contain the microorganism cells entrapped therein.

By and large, immoblization of viable microorganism cells in (calcium) alginate beads is well known to the art, as witness for example, the description of immobilizing yeast cells in calcium alginate in U.S. Pat. No. 3,733,205. The immobilization technique herein employed also has been described in the technical literature, see White et al., J. Inst. Brew. July-August 1978, Vol. 84, pp. 228230, but mostly the art describes laboratory scale procedures. Since large scale production of particulate (calcium) alginate gel is contemplated herein it may be mentioned that a pump which pumps a solution of alginate and suspended cells through a multitude of nozzles into a $CaCl_2$ solution producing thereby many hundred liters of gel beads per hour constitutes an advantageous mode.

The compressibility of the alginate gel beads will generally increase in some proportion to the concentration of alginate in the alginate solution, and with the concentration of microorganism cells suspended in the alginate solution, which in effect means that lower concentration of alginate and higher concentration of microorganism cells in the alginate solution create relatively a more compressible gel product, as will use of lower quality alginate grades. In any event, appropriate care should be taken in operation of a bed or column containing alginate gel particles to avoid compressing the particles too much. Desirably, the bed height of alginate particles should be below about 3 meters to avoid sudden blockages in the column through collapse of the discrete alginate gel particles into a solid mass.

Shelf Life

The usual approach to consideration of shelf life for an immobilized enzyme or microorganism, has been to dry the product, as witness the commentary posed by U.S. Pat. No. 3,733,205 about drying the microorganism containing alginate beads or to use the immobilized microorganism immediately (White et al. supra).

For practice of this invention, a different approach has been taken. The alginate gel particles are never dried. They are prepared, of course, in an aqueous medium, and thereafter are always maintained immersed in an aqueous medium. For storage and shipment, the alginate particles are immersed in an aqueous medium suited to maintaining viability of the microorganism, i.e., a resting medium. As has already been pointed out a sterile resting medium is preferred. Also preferred for the resting medium is a growth medium for the *L. oenos*. The wet alginate particles may be from 25 and 100%, preferably about 50% of the gross volume of the cells and resting medium.

Thus, within hours after formation of the alginate gel in the calcium chloride solution, the gel particles are transferred to a resting medium, such as for example, sterile grape juice (pH adjusted to about 3.5) containing 5-12% ethanol, the most preferred resting medium.

Of course, any (sterile) growth medium for cultivation of *L. oenos* may be used for protecting the alginate immobilized cells, although grape juice is one of the most preferred media. Desirably, the resting medium contains therein from 5–12% v/v ethanol and is adjusted to a pH in the range of pH 3.0–4.5. Grape juice with 5–12% alcohol in part, acclimatizes the *L. oenos* to the alcoholic wine milieu in which the cells will be employed. In general, the resting medium should be anaerobic, and may be degassed before use; an inert ($CO_2$ or $N_2$) atmosphere may be placed over the stored in resting medium gel particles.

At 4°–8° C. the so immobilized *L. oenos* cells survive storage in sterile or filtered grape juice for over a month. It is believed by the inventors hereof that storing the alginate gel particles immersed in a resting medium retains a maximum level of cell viability.

PROCESS CONSIDERATIONS

Since storage and shipment of *L. oenos* cells immobilized in particulate alginate gel in a resting medium, such as grape juice, is herein contemplated, employment of the gel for its malolactic activity requires first that the resting medium be removed and replaced by wine. Thus, in a preferred embodiment of the present invention, the alginate beads are wet packed into the reactor, e.g., a column, along with the resting medium. In due course, the resting medium is replaced by wine to be deacidified by the immobilized microorganism cells.

One characteristic of *L. oenos* worthy of note is that many strains of this microorganism are susceptible to the presence of $SO_2$. Indeed, it has been found that when the substrate is grape juice containing 10% ethanol and 500 to 600 ppm of L-malate, the activity of the alginate immobilized *L. oenos* cells remains unchanged for weeks but when the grape juice substrate is abruptly changed to wine containing $SO_2$, for instance a wine with about 90 mg of $SO_2$ per liter, the malolactic activity of the gel particles decrease rapidly, implying thereby a sudden virtually complete kill of the microorganism cells. If, however, the $SO_2$ level in the substrate is raised gradually, as for example, by a gradually increasing proportion of sodium sulphite in either a resting medium substrate or in an otherwise low $SO_2$ wine substrate, or by gradually substituting an $SO_2$ containing wine for a resting medium substrate, complete sudden death of the cells no longer takes place upon changing the substrate to an $SO_2$ containing wine. In one exemplary instance, using a white Côte du Rhône 1977 with 30 mM L-malate added, pH adjusted to 3.5, an alginate gel bead column maintained between 15 and 20 percent of its original lactate productivity (measured in grape juice) for a thousand hours of wine treatment.

Accordingly, practice of this invention with *L. oenos* strains susceptible to sulphur dioxide involves displacement of the resting medium by a substrate (which may be the same resting medium) containing dissolved $SO_2$ in gradually increasing concentrations until an $SO_2$ content normally present in wines has been achieved, and only thereafter completely substituting the ($SO_2$ containing) wine for the substrate, and then passing wine through the column for deacidification. Acclimatizing the particulate gel to a total $SO_2$ content about 100 mg of $SO_2$ per liter of substrate is suggested.

As has already been indicated, preferred practice of the present invention involves deacidification of wine by passage of the wine through a column containing a fixed bed of alginate immobilized *L. oenos*. The particular advantages of column treatment are that the level of conversion can be controlled quite exactly by adjustment of bed height and residence time for wine in the bed (i.e., fluid velocity). Of course, further adjustment can be provided by variations in the concentration of microorganism cells in the alginate particles, e.g., beads. By and large, the malolactic conversion is rapid, which in itself is an advantage since deleterious microorganisms that may be in the wine, such as Pediococci are not given opportunity to compete.

The desirability of close control over deacidification, as is possible in a column process, can be appreciated from consideration of what can take place during an ordinary (uncontrolled) *L. oenos* process. The primary stage of the ordinary *L. oenos* process is conversion of malic acid to lactic acid. When no malic acid remains, a second stage which then commences is fermentation of sugar with $CO_2$ development and creation of organoleptically unwanted by-products. In the column process, the wine is removed from the bed of immobilized microorganism cells when the primary stage of the *L. oenos* process has been carried out, thereby avoiding any secondary stage fermentation.

For further understanding of the practice of the present invention, following are specific examples thereof.

EXAMPLE 1

Cultivation of *L. oenos*.

The *L. oenos* was fermented anaerobically at 20°–30° C. in flasks for one week with mild agitation on the following medium. (The fermentation time could be reduced to 2–5 days.)

Difco Micro Inoc. Broth (320-02-1): 20 g/l
Difco Folic Acid Assay Med. (318-15-0): 20 g/l
pH is adjusted to 4.2–4.5 with malate ca.: 6 g/l Three different strains of *L. oenos* cultivated in the medium described above were tested for malolactic activity. The test results are set forth in the following Table.

TABLE 1

| Strain | Activity ($\mu$/ml) |
|---|---|
| DSM 20252 | 79 |
| Leuco Start | 147 |
| Teufen | 159 |
| ML-34 | 80 |

EXAMPLE 2

Immobilization

One kg of cell sludge (about 15% dry matter) from a fermentation carried out as described in Example 1 (strain Teufen) was mixed with 8 kg of 5% sodium alginate (Satialgine S-550) solution that had been autoclaved at 120° C. for 20 minutes. Beads of alginate gel were formed by pumping the mixture through a 1 mm orifice to drip into aqueous 2% calcium chloride solution of pH 4.5 at a rate of about 1 liter of alginate solution cell suspension per hour at room temperature, forming beads of about 2 mm diameter. After two hours of residence in the calcium chloride solution, the alginate beads were washed with sterile water and transferred wet to sterile filtered grape juice containing 10% ethanol, pH 3.5. The alginate beads and grape juice were stored at 4° C. Tests showed a degree of viability approximating 100% for the microorganism cells after storage for a week.

For assaying the initial malolactic activity of fermentation broth, a sample of cell sludge or redissolved immobilized cells (alginate gel dissolved by 1 hour of stirring in 0.2 M citrate phosphate, pH 5) is incubated for 1 hour in a shaking thermostat bath at 30° C. with 30 mM L-malate, 1.67 mM NAD and 0.7 mM $MnCl_2$ in 0.4 M phosphate buffer pH 6.0.

The produced lactate is then determined spectrophotometrically at 340 nm according to Bergmeyer in Methods of Enzymatic Analysis, AP, 2nd ed., Vol. 3, p. 1467 by using lactate dehydrogenase and excess NAD in hydrazine/glycine buffer pH 9.0. (The same procedure can be used for determination of residual malate if lactate dehydrogenase is replaced with malate dehydrogenase.)

1 malolactic activity unit is defined as 1 micromol L-malate converted per minute.

EXAMPLE 3

Deacidification of Wine

Six kg of the alginate beads prepared as in Example 2, that had been stored for one week at 4° C. were packed into a laboratory reactor column 12 cm in diameter to form a fixed bed 80 cm high; the total packed bed volume being about 9 liters. The column was connected up so that substrate could be pumped upflow through the column at about 20° C., then passed by way of a cooler to a storage container.

With grape juice supplied with 30 mM L-malate per liter and 10% ethanol pH 3.5 for substrate, the malolactic activity of the immobilized cells remained unchanged for weeks. However, when the substrate was abruptly changed to a wine containing about 90 mg of sulphur dioxide per liter the activity rapidly decreased ($T_{\frac{1}{2}}$ approximately 40 hours). In a short period of time, essentially no malolactic activity was evidenced.

In a second run, the grape juice supplied with the L-malate and 10% ethanol was changed so as to contain first 20 mg $SO_2$, at which content no decrease in activity was noticed. Subsequently, the substrate was dosed to 40 mg of $SO_2$ per liter, then 50, then 75, then 100. Thereafter, over a 200 hour changeover period the grape juice substrate was changed over to an (acid) wine containing about 80 mg of $SO_2$ and of 10% ethanol content. During the course of $SO_2$ acclimatization and changeover to the wine substrate, the malolactic activity of the immobilized cells declined sharply but not completely. Malolactic activity stabilized at about 20% of original activity, and thereafter, declined slowly over a 1000 hour period, even though in the midst of this period a different wine was substituted, the second wine containing 100 mg of total $SO_2$ per liter and 12% ethanol.

The productivity of the immobilized cells was estimated at about 0.4 liters of wine per liter of immobilized cell per hour with about 50% conversion of 30 mmol L-malate per liter.

EXAMPLE 4

This Example illustrates the differences in malolactic activity that can be expected from immobilization of *L. oenos* in different alginates.

Wet cells (Teufen Strain) were mixed 1:9 with either 5% or 3% solution of sodium alginate and the mixture dripped into 2% $CaCl_2$ solution of pH 4.5. After 2 hours the resulting alginate beads were transferred to grape juice of pH 3.5 and then packed in a column.

The activity measurements of the alginate beads are tabulated below.

TABLE 2

Immobilized Leuconostoc Oenos Preparations

| Matrix/ Method | Gel % | Sludge % | Initial Activity in Ferm. Broth μ/l(pH 5, 30° C.) | Initial Activity in gel beads after dissolving (pH 5,30° C. μ/l) | Column Activity of gel beads mmol/h.l (grape juice pH 3.5 25° C.) |
|---|---|---|---|---|---|
| BDH alginate | 4.5 | 10 | 55 | 6,000 | 45 |
|  |  |  | 70 | 8,000 | 43 |
| Satialgine S 550 | 4.5 | 10 | 80 | 5,500 | 25 |
|  |  |  | 65 | 5,000 | 21 |
|  |  |  | 55 | 4,500 | 22 |
| Satialgine S 1100 | 2.7 | 10 | 80 | 3,500 | 19 |

Column Activity of Immobilized Leuconostoc Cells

A 2.5 cm diameter column is filled with a known amount of gel (e.g., 50 g). Milliporefiltered grape juice substrate containing 30 mM L-malate and 10% ethanol and adjusted to pH 3.5 is stored at 4° C. and thermostatted to 25° C. at the column inlet. The column is run with a constant malate conversion of 90% until a steady state column malolactic activity is obtained as determined from lactate produced or L-malate converted.

The beads from Satialgine S-550 were pressure tested. They blocked at bed heights above about 2.5-3 meters.

EXAMPLE 5

This example illustrates an alternative method for acclimatizing the cells to the $SO_2$ content of wine.

Alginate beads prepared as described in Example 2 were charged into a 40 ml column; then the column was started on grape juice supplied with 10% ethanol and 40 m ML-malate per liter pH adjusted to 3.5 The substrate was gradually changed over a 400 hour period to red Côte du Rhône having 30 mM of L-malate added, pH adjusted to 3.5. The column was then run with wine for an additional 1000 hours. The wine contained 85 mg total $SO_2/l$, 30 mg free $SO_2/l$.

The results are tabulated below.

TABLE 3

| Flow ml/h (space vel.) | Malate mM | Lactate mM | Conversion % |
|---|---|---|---|
| Before treatment | 34 | 14 | — |
| 15 ml/h (0.4) after 900 hours | 1 | 43 | 95 |

EXAMPLE 6

Two bottles of California red wine that had not undergone spontaneous malolactic conversion even after two years were treated by passing through a 40 ml column with alginate-entrapped cells prepared as described in Example 2, and acclimatized to wine as described in Example 5.

The California wine substrate had 16 mg free $SO_2/l$; 157 mg total $SO_2/l$; and pH about 3.5.

TABLE 4

| Flow ml/h (Space Vel.) | Malate mM | Lactate mM | Conversion % |
|---|---|---|---|
| Before treatment | 11.5 | 1.5 | — |

TABLE 4-continued

| Flow ml/h (Space Vel.) | Malate mM | Lactate mM | Conversion % |
|---|---|---|---|
| 20 (0.5) | 0 | 13 | 100 |
| 40 (1.0) | 1 | 12 | 91 |
| 60 (2.5) | 2 | 11 | 83 |

Four gallons of a different California red wine was treated on a 500 ml column with the following results.

TABLE 5

| Flow ml/h (Space Vel.) | Malate mM | Lactate mM | Conversion % |
|---|---|---|---|
| Untreated | 7.5 | 1 | — |
| 400 ml/h (0.8) | 1 | 8 | 90 | pH of the treated wine had increased from 3.0 to 3.3 and the sugar content had increased slightly from 6.5 g/l to 7-7.15 g/l (attributed to rest sugar from the grape juice).

EXAMPLE 7

A pilot plant study carried out on Swiss wines employed about 9 liters of Teufen Strain of *L. oenos* containing alginate beads (including 3.5 liter interspace) made as described in Example 2 then stored for one week at 4° C. in a 12 cm×100 cm glass column. The beads seated on a glass sinter and the space above the beads was filled with glass wool. A rubber stopper with four outlets capped the column. Substrate was pumped upflow through the column at 20° C., then to a cooler, and afterward to storage. The results are tabulated below.

TABLE 6

| Substrate | Flow l/h (space vel.) | Malate mM | Lactate mM | Conversion % |
|---|---|---|---|---|
| White grape juice pH 3.5, 10% ethanol | Before Treatment | 58 | 3 | — |
|  | 15 (1.7) | not. det. | 56 | 91 |
| White wine 'Chasselas' pH 3.4, 23 mg free SO$_2$ 48 mg total SO$_2$ no rest sugar | Before Treatment | 30 | 2 | — |
|  | 7 (0.8) | 1 | 32 | 97 |
| Red wine 'Gamay' pH 3.5, 11 mg free SO$_2$ 37 mg total SO$_2$ no rest sugar | Before Treatment | 26 | 2 | — |
|  | 5 (0.6) | 0 | 28 | 100 |

The collected wine was then subjected to (normal) processing of SO$_2$ addition, tartrate removal, storage and bottling. By comparison with the same type of wine which had undergone spontaneous malolactic conversion, it was found that the column treated wines had satisfactory organoleptic properties.

We claim:

1. A process for deacidifying wine with alginate gel particles containing living cells of *Leuconostoc oenos* immobilized herein, and said alginate gel particles being immersed in an aqueous sterile resting medium for maintaining viability of the microorganism which process comprises:
   i. preparing a bed of said alginate gel particles, then
   ii. displacing gradually said resting medium in the alginate gel particles with wine thereby conditioning the living cells to wine and thereafter
   iii. passing wine through said bed to deacidify the wine by the malolactic activity of the microorganism cells.

2. The process of claim 1 including prior to treating wine, subjecting the alginate gel particles and the living cells therein to ever increasing SO$_2$ levels, whereby the living cells become conditioned to the presence of SO$_2$ in the wine.

3. The process of claim 1 wherein said resting medium is grape juice containing about 5-12% ethanol.

4. A particulate composition adapted for deacidifying wine comprising alginate gel particles containing therein living cells of *Leuconostoc oenos*, said gel being immersed in an aqueous sterile resting medium for maintaining viability of the microorganism, said resting medium being sterile grape juice containing 5-12% ethanol.

5. The method of preparing a composition adapted for deacidifying wine which comprises:
   i. cultivating a strain of *Leuconostoc oenos* and collecting the *Leuconostoc oenos* cell sludge, then
   ii. dispersing the cell sludge in an alginate solution, thereafter
   iii. passing the cell sludge containing alginate solution to an aqueous Ca salt solution whereby the alginate solution converts into an alginate gel, and
   iv. transferring the alginate gel from the salt solution to a sterile resting medium comprising grape juice containing 5-12% ethanol for maintaining viability of the microorganism.

6. A process for deacidifying wine which comprises contacting wine with a bed of alginate gel particles said alginate gel particles containing living cells of *Leuconostoc oenos* immobilized therein, whereby the malolactic activity of the cells deacidifies the wine, said process commencing with said alginate gel particles initially immersed in an aqueous sterile resting medium for maintaining viability of the microorganism and gradual substitution of wine to be treated for said resting medium.

* * * * *